United States Patent [19]

Furey

[11] 4,090,760

[45] May 23, 1978

[54] ELECTRICAL CONNECTION SYSTEM

[75] Inventor: Robert J. Furey, Valdosta, Ga.

[73] Assignee: Bunker Ramo Corporation, Oak Brook, Ill.

[21] Appl. No.: 729,820

[22] Filed: Oct. 5, 1976

[51] Int. Cl.[2] .......... H01R 13/62; A61N 1/04

[52] U.S. Cl. .......... 339/61 R; 128/416; 128/DIG. 4

[58] Field of Search .......... 339/61, 74, 75 P, 91 R; 128/2.06 E, 2.1 E, 404, 416, 417, 418, DIG. 4

[56] References Cited

U.S. PATENT DOCUMENTS

| | | | |
|---|---|---|---|
| 2,850,711 | 9/1958 | Terlinde | 339/74 R |
| 2,895,479 | 7/1959 | Lloyd | 128/417 |
| 3,085,577 | 4/1963 | Berman | 128/DIG. 4 |
| 3,281,754 | 10/1966 | Cadwallader | 339/61 K |
| 3,937,546 | 2/1976 | Clewes | 339/61 R |
| 4,029,381 | 6/1977 | Tarrall | 339/61 R |
| 4,030,796 | 6/1977 | Patzer | 339/61 R |

FOREIGN PATENT DOCUMENTS

| | | | |
|---|---|---|---|
| 2,210,844 | 9/1973 | Germany | 339/91 R |

*Primary Examiner*—Neil Abrams

*Attorney, Agent, or Firm*—Hill, Gross, Simpson, Van Santen, Steadman, Chiara & Simpson

[57] ABSTRACT

An electrical connector system has a contact member with a tunnel portion and spaced, vertical contact pillars secured within the tunnel portion. Extensions of the contact pillars bind the contact member to a metal plate in staple-like fashion. The metal plate is preferably useful as an electrode for medical electronic equipment. A cable connector which snap-latches directly to the contact pillars has an encasement formed of semi-flexible arm members joined at a base portion. A wedge-shaped frontal portion is positioned at the end of each arm member such that points of the adjacent frontal portions are spaced less than the spacing between the contact member contact pillars. A notch is provided rearward of the frontal portions on each of the arms for latching to each of the contact pillars when the cable connector is pushed into the tunnel portion of the contact member. A contact strip positioned within each arm member has a portion which is positioned within the notch adjacent the bottom portion thereof for electrical contact with the pillars.

4 Claims, 5 Drawing Figures

ELECTRICAL CONNECTION SYSTEM

RELATED APPLICATION

In related, copending application, U.S. Ser. No. 711,456, filed Aug. 11, 1976, the use of a tunnel-shaped contact member having internally spaced vertical contact pillars is disclosed for the purpose of connecting a cable connector to a metal plate. In that application, cable connector probes are described which have hook-shaped contact clips which positively engage the contact pillars. Typically, the tunnel-shaped contact member is fastened by staple-like attachment to a metal pad used as a body electrode for connection of sensing cables for medical equipment. Since the metal plate to which the tunnel-shaped contact member is attached may be moved into different positions as the patient moves about, longitudinal and lateral stresses are applied at the point of electrical contact between the probe and the contact member. The use of hook-shaped contact wires, although adequate for many applications, may not be adequate from an electrical and mechanical standpoint when used in connection with medical pad electrodes.

BACKGROUND OF THE INVENTION

1. Field of the Invention

This invention relates to electrical connection systems and more particularly to snap-latching of cable connectors to contact members.

2. Description of the Prior Art

Previously, electrical cables from medical equipment were attached to metal plates serving as body electrodes by use of a clothing snap type fastening system. Such systems have sometimes been found unacceptable in view of the lateral and longitudinal stresses applied at the point of connection. Consequently, it was suggested to employ a tunnel-shaped contact member which is attached in staple-like fashion to the metal plate of the body electrode. (See discussion above concerning related application Ser. No. 711,455).

It has been proposed by others to utilize a U-shaped latch member having resilient arms which may be squeezed together to permit insertion into a tunnel-shaped member. In the suggested latch, barbs were provided on the ends of the arms of the U-shaped member which clamped onto lateral edges of the tunnel in a plastic-to-plastic connection. A disadvantage with such devices is difficulty of providing a good electrical connection since the plastic-to-plastic contact between the tunnel member and the cable connector inhibits a solid metal-to -metal contact. Furthermore, when such a cable connector is laterally stressed, the metal contacts separate due to the plastic-to plastic abutment adjacent the electrical contact. A further disadvantage results since the plastic-to-plastic abutment may reduce the electrical contact force between the metal contact members. Finally, it would be desirable to have a snap-latch cable connector which automatically latches to contact pillars of a tunnel contact member when the cable connector is pushed therein without the need for prior squeezing of the connector arm.

SUMMARY OF THE INVENTION

It is an object of this invention to provide a cable connection system in which a cable connector maintains solid electrical contact during lateral stress of the cable connector with respect to the contact member.

It is a further object of this invention to utilize stiff contact pillars for both electrical contact and for mechanical cable connector support.

It is another object of this invention ot provide appropriate electrical contacts and a cable connector for use with a tunnel-shaped contact member.

It is a further object of this invention to provide a cable connector which will snap-latch to a tunnel-shaped contact member having vertically spaced contact pillars without the need for squeezing of the arms on the cable connector.

It is yet another object of this invention to provide a cable connector in which effective electrical contact is maintained despite the application of lateral and longitudinal stresses to the cable connector.

In the electrical connector system according to this invention, a contact member is provided having a tunnel portion and spaced, exposed, vertical contact pillars secured within the tunnel portion. The tunnel portion of the contact member is formed by spaced apart planar top and bottom members with end support pillars therebetween. Each support pillar is adjacent a contact pillar and spaced therefrom. A side width of each of the support pillars is less than the length of the tunnel.

A cable connector for latchably engaging the contact pillars has a plastic encasement formed of resilient, semi-flexible arm members joined at a base portion. A wedge-shaped frontal portion is provided at the end of each arm member. A laterally open notch means rearward of the frontal portion latches to each of the contact pillars but not to other portions of the contact member. The contact strip is positioned within each arm member such that a portion of the strip is accessible to the pillar adjacent a bottom portion of the notch means.

Since the wedge-shaped portions of the cable connector have points which are spaced less than the spacing of the vertical contact pillars, the cable connector may be pushed into latching engagement with the contact member since the contact member contact pillars ride along the wedge-shaped portions to squeeze the arms together until latching with the notches. Since the notches latch only to the contact pillars, the electrical contact developed within the notches between the contact strips and the contact pillars is maintained despite lateral or longitudinal stresses applied to the cable connector. By providing substantial, stiff, contact pillars, the pillars provide both electrical contact and mechanical support.

DESCRIPTION OF THE PREFERRED EMBODIMENTS

Figures 1, 2, 3, 4, 5:
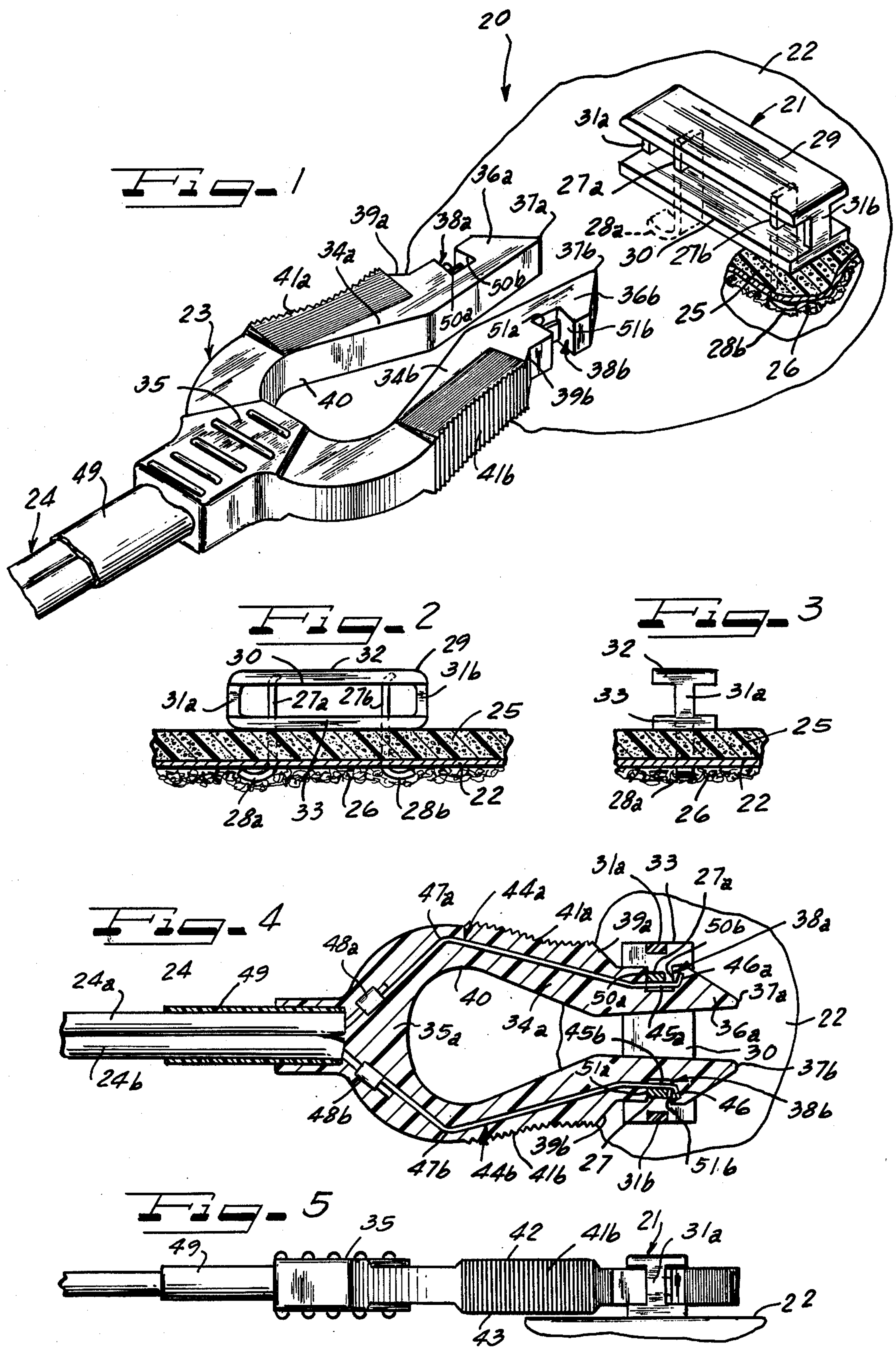
FIG. 1 is a perspective view of the electrical connection system of this invention.
FIG. 2 is a front view of a contact member of this invention.
FIG. 3 is an end view of the contact member of FIG. 2.
FIG. 4 is a plan view of a cable connector of this invention.
FIG. 5 is a side view of the cable connector of FIG. 4.

As shown in FIG. 1, a snap-latching electrical connection system 20 of this invention consists of a tunnel-shaped contact member 21 which is fastened by staple-like attachment through a foam rubber pad 25 to a metal plate 22, such as a body-applied electrode for medical equipment. A tube conductor cable 24 connects through a cable connector 23 to the contact member 21.

As more clearly shown in FIGS. 2 and 3, a foam rubber pad 25 is arranged on one side of the metal plate 22 and a fiber 26 with electrode jelly is arranged on the other side thereof. The contact member 21 has spaced vertical contact pillars 27*a,b* positioned within a tunnel section 29 of the contact member. In the form illustrated each of the contact pillars has a rectangular cross-section and consists of nickel for galvanic compatibility with an Inconel metal plate 22. Such contact pillars exhibit a low contact resistance when biased with minimum force against contact strips of a cable connector, as described below. A normal force of 100 grams supplies adequate contact force with minimum contact resistance.

Staple-like attachment arms 28*a,b* are formed as extensions of the contact pillars 27*a,b*. These attachment arms are deformed up against the metal plate 22 so as to pull the contact member 21 into staple-like, conductive, engagement with the foam pad 25 and plate 22. The resilient foam pad 25 is compressed during the stapling operation to provide "stored energy" to insure conductive engagement between the contact pillars 27*a,b* and plate 22.

The tunnel section 29 has a rectangular tunnel 30 shaped by top and bottom planar members 32 and 33 separated by side support pillars 31*a,b*. By providing support pillars 31*a,b* rather than a wall along the entire depth of the tunnel 30, the four corners of the tunnel remain open such that when the cable connector 23 is inserted into the tunnel 30, portions of the cable connector 23 do not rub against any portion of the tunnel section 29, especially during lateral stresses applied to the cable connector 23.

As shown most clearly in FIGS. 4 and 5, the snap-latch cable connector 23 has flexible tynes or arms 34*a,b* which are joined together at a base portion 35 to form a horse-shoe shaped encasement. This encasement is preferably formed of a thermoplastic carbonate-linked polymer such as Lexan, a trademark of the General Electric Co., Schenectady, N.Y. Such a material is preferred since it is sufficiently stiff so that repeated squeezing of the arms 34*a,b* does not cause a permanent deformation. Other materials such as polypropylene are also acceptable but do not have the preferred stiffness or clarity of Lexan.

Wedge-shaped frontal portions 36*a,b* are provided on each of the arms 34*a,b*. These frontal portions permit insertion of the cable connector 23 into the contact member without squeezing of the arms since points 37*a,b* on the frontal portions 36*a,b* are spaced slightly less than the spacing of the contact pillars 27*a,b*. Consequently, the contact pillars 27*a,b* slide along the wedge-shaped portions 36*a,b* to automatically squeeze the arms 34*a,b* together.

Notches 38*a,b* are provided rearward of the frontal portions 36*a,b*. Side walls 50*a,b* and 51*a,b* are slanted inwardly to promote retention of the contact pillars. The notches also have an average width which is slightly greater than the contact pillars 27*a,b* and a depth which is slightly greater than the thickness of the contact pillars. If the notches were too deep, portions of the arms 34*a,b* would contact the tunnel support pillars 31*a,b* in undesirable fashion. Also, the width of the notches 38 should be large enough to retain the contact pillars 27*a,b* but not so large as to permit a lateral twisting of the connector relative to the contact member. With the notch shape of this invention, lateral deflection of the cable connector does not result in any plastic-to-plastic binding which could cause the electrical contacts to lift off of one another. Furthermore, an inclined shoulder 39*a,b* is provided on each of the arms rearward of the notches 38*a,b* to permit portions of the arms within the tunnel section 29 to have a reduced width. Consequently, edge portions of the arms are prevented from contacting the support pillars 31*a,b* during lateral deflections of the cable connector 23.

As shown most clearly in FIG. 4, a horse-shoe shaped cutout area 40 is formed between the arms 34*a,b*. It has been determined that this shape provides adequate flexing of the arms when the arms consist of Lexan or polypropylene. Also shown in FIG. 4 are curved finger grip areas 41*a,b* formed on built-up portions 42 and 43 (See FIG. 5). These grips provide a convenient surface for squeezing the arms together to ease the snap-latch insertion of the cable connector 23, and to release the snap-latch for removal of the cable connector 23.

The cable connector electrical contacts are shown most clearly in FIG. 4 as strips 44*a* and 44*b*. These strips are preferably copper-berryllium with tin plating for oxidation protection and low contact resistance and molded into the arms 34*a,b*. Contact portions 45*a* and 45*b* are positioned within the notches 38*a,b* just above the notch floors. Upturned lips 46*a,b* at the ends of the contact strips 44*a,b* are molded between the wedge-shaped frontal portions 36*a,b* and the notches 38*a,b*. These provide longitudinal and lateral support for the contact portions 45*a,b* such that when these contact portions are biased against the contact pillars 27*a,b* the strips are held securely in position.

Contact strips 44*a,b* have bends 47*a,b* in the base portion 35 of the encasement such that the ends of the strips are in proximity to cable wires 24*a,b* to permit an automatic splicing by crimping at 48*a,b*. A strain relief 49 consisting of flexible tubing is mounted in the base portion 35 in order to support the cable 24.

In one preferred embodiment of this invention the contact member contact pillars 27*a,b* have a rectangular cross section of approximately 0.03 × 0.06 inch. Such pillar dimensions provide the needed stiffness to support the cable connector during longitudinal and lateral stresses. Other approximate dimensions may be 0.09 × 0.06 inch for the cross section of the support pillars 31*a,b*; 0.25 × 0.81 inch for the planar members 32 or 33; 0.09 inch for the distance between the support pillars 31*a,b* and a corner of the tunnel 30; and 0.10 inch spacing between the contact pillars 27*a,b* and the support pillars 31*a,b*.

For the cable connector 23 approximate dimensions for the notches 38*a,b* are 0.078 to 0.093 width (increasing width with depth); and 0.093 inch depth. The contact portions 45*a* and 45*b* are spaced about 0.062 inch from the tops of the notches and the contact strips 44*a,b* have a width of approximately 0.062 inch.

To operate the connection system of this invention, the cable connector 23 is manually inserted into the tunnel-shaped contact member 21 by positioning the points 37*a,b* of the frontal portions 36*a,b* between the contact pillars 27*a,b*. As the cable connector is thrust into the contact member, the arms 34*a,b* are automatically flexed towards one another until the notch portions 38*a,b* spring out around the contact pillars 27*a,b*. If lateral or longitudinal stresses are now applied to the cable connector 23, it will be noted that the cable connector is retained in position solely by the contact pillars *27a,b*. Consequently, these stresses do not result in an opening of the electrical contacts. The upper and lower planar members 32 and 33 of the tunnel section 29 serve to support the cable connector 23 against vertical stresses.

Although various minor modifications may be suggested by those versed in the art, it should be understood that I wish to embody within the scope of the patent warranted hereon, all such embodiments as reasonably and properly come within the scope of my contribution to the art.

I claim as my invention:

1. An electrical connector system comprising:

a. a contact member having a tunnel portion and spaced, vertical contact pillars secured within the tunnel portion;

b. a cable connector latchably engageable to said contact pillars, and having an encasement formed of resilient arm members joined at a base portion;

c. a frontal portion at the end of each arm member;

d. a notch means rearward of the frontal portion for latching to each of the contact pillars but not other portions of the contact member;

e. a contact strip positioned within each arm member, a portion of said strip being positioned in and exposed in said notch means adjacent a bottom portion thereof; and f. the tunnel portion being formed by spaced apart, planar top and bottom members with end-support pillars therebetween, each support pillar being adjacent a contact pillar and spaced therefrom, a side width of each of said pillars being less than the length of the tunnel.

2. The system of claim 1 in which the vertical contact pillars of the contact member extend outwardly for staple-like attachment to a metal plate.

3. The system of claim 1 in which the contact pillars and contact strips have generally flat surfaces for abutting electrical contact.

4. The system of claim 1 in which a shoulder means is formed on the outside of each arm member rearward of each notch for a transition in arm thickness from the portions of the arm member adjacent the notch to portions of the arm rearward of the notch.

* * * * *